US009827188B2

(12) United States Patent
Du et al.

(10) Patent No.: US 9,827,188 B2
(45) Date of Patent: *Nov. 28, 2017

(54) COMPOSITIONS COMPRISING AMPELOPSIS GROSSEDENTATA AND ALBIZIA JULIBRISSIN EXTRACTS

(71) Applicant: Johnson & Johnson Consumer Inc., Skillman, NJ (US)

(72) Inventors: Hua Du, Shanghai (CN); Yan Li, Shanghai (CN); Tao Liu, Shanghai (CN); Yingxin Ma, Shanghai (CN)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,573

(22) Filed: Sep. 24, 2015

(65) Prior Publication Data

US 2017/0042788 A1     Feb. 16, 2017

(30) Foreign Application Priority Data

Aug. 14, 2015   (CN) .......................... 2015 1 0500612

(51) Int. Cl.

| A61K 8/97 | (2017.01) |
|---|---|
| A61Q 19/00 | (2006.01) |
| A61Q 19/08 | (2006.01) |
| A61K 9/00 | (2006.01) |
| A61K 36/48 | (2006.01) |
| A61K 36/87 | (2006.01) |
| A61Q 5/02 | (2006.01) |
| A61Q 5/12 | (2006.01) |
| A61Q 19/10 | (2006.01) |

(52) U.S. Cl.
CPC .............. *A61K 8/97* (2013.01); *A61K 9/0014* (2013.01); *A61K 36/48* (2013.01); *A61K 36/87* (2013.01); *A61Q 19/007* (2013.01); *A61Q 19/08* (2013.01); *A61K 2800/5922* (2013.01); *A61Q 5/02* (2013.01); *A61Q 5/12* (2013.01); *A61Q 19/10* (2013.01)

(58) Field of Classification Search
CPC .... A61K 2300/00; A61K 36/48; A61K 36/87; A61K 2800/5922; A61K 8/97; A61K 9/0014; A61Q 19/007; A61Q 19/08; A61Q 19/10; A61Q 5/02; A61Q 5/12
See application file for complete search history.

(56) References Cited

U.S. PATENT DOCUMENTS

| 7,442,391 B2 | 10/2008 | Koganov |
|---|---|---|
| 7,452,547 B2 | 11/2008 | Lambino et al. |
| 7,473,435 B2 | 1/2009 | Koganov |
| 7,537,791 B2 | 5/2009 | Koganov |
| 2006/0141014 A1 | 6/2006 | Eknoian et al. |
| 2007/0196523 A1 | 8/2007 | Koganov |
| 2009/0241242 A1 | 10/2009 | Beatty et al. |
| 2010/0119469 A1* | 5/2010 | Wu .......................... A61K 8/97 424/73 |
| 2012/0157939 A1* | 6/2012 | Loy ..................... A61K 36/8967 604/303 |
| 2015/0017269 A1 | 1/2015 | Fournial et al. |

FOREIGN PATENT DOCUMENTS

| CN | 1103287 | 6/1995 |
|---|---|---|
| CN | 1977926 | 6/2007 |
| CN | 101336987 A * | 1/2009 |
| CN | 101422538 | 5/2009 |
| CN | 102038675 | 5/2011 |
| CN | 102100656 | 6/2011 |
| CN | 102552092 | 7/2011 |
| CN | 102716401 | 10/2012 |
| CN | 102771594 | 11/2012 |
| CN | 102772587 | 11/2012 |
| CN | 102973471 | 3/2013 |
| CN | 103405731 | 11/2013 |
| CN | 103860987 | 6/2014 |
| JP | 2000143488 | 5/2000 |
| JP | 200109783 | 4/2001 |
| JP | 2001097873 | 4/2001 |
| JP | 2002308790 | 10/2002 |
| JP | 2002370962 | 12/2002 |
| JP | 2002370962 A * | 12/2002 |
| JP | 2003192566 | 7/2003 |
| JP | 2004120658 | 7/2004 |
| JP | 2004262852 | 9/2004 |
| JP | 2007204414 | 8/2007 |
| JP | 2008290970 | 12/2008 |
| JP | 2009242296 | 10/2009 |

(Continued)

OTHER PUBLICATIONS

Japanese Patent Document JP 2002/370962, 2002, English Translation acquired from Espacenet May 2016.*
Japanese Patent Document JP 2009/242296, 2009, English translation acquired from Espacenet May 2016.*
Shi et al. CN 101336987 A, Espacenet English translation, downloaded Mar. 2017.*
Akerlof, G., "Dielectric Constants of Some Organic Solvent-Water Mixtures at Various Temperatures", The Journal of the American Chemical Society, vol. 54, No. 11, pp. 4125-4139 (Nov. 1932).
Albizza, Chinese Herbs, www.acupuncture-and-chinese-medicine.com/albizza.html Retrieved Dec. 9, 2015.
Ando, H., et al. "Quasi-Drugs Developed in Japan for the Prevention or Treatment of Hyperpigmentary Disorders", International Journal of Molecular Science, vol. 11, pp. 2566-2575 (2010).

(Continued)

*Primary Examiner* — Mark V Stevens

(57) ABSTRACT

A composition for applying to skin in need of treatment for skin barrier restoration, hydration and moisturization, the composition comprising extracts of *Ampelopsis grossedentata* and *Albizia julibrissin*. Also provided are methods for treating skin in need of skin barrier treatment, methods of treating skin to reduce the signs of aging and methods of treating skin to reduce the signs of inflammation with a composition comprising extracts of *Ampelopsis grossedentata* and *Albizia julibrissin*.

14 Claims, No Drawings

(56) References Cited

FOREIGN PATENT DOCUMENTS

| JP | 2009242296 A | * 10/2009 |
| JP | 2010235548 | 10/2010 |
| KR | 20100041243 | 4/2010 |
| WO | WO2005046630 | 5/2005 |

OTHER PUBLICATIONS

Baumann, L., "Skin Ageing and Its Treatment", J. Pathology, vol. 211, pp. 241-251 (2007).
deGuertechin, L., "Classification of Surfactants", Handbook of Cosmetic Science and Technology, Edited by A. Barel, pp. 431-450 (2001).
Du, Q., et al., "Preparative Separation of Flavonoid Glycosides in Leaves Extract of *Ampelopsis grossedentata* Using High-Speed Countercurrent Chromatography", Journal of Chromatography, vol. 1040, pp. 147-149 (2004).
Eckert, R., et al., "Transglutaminase Function in Epidermis", The Journal of Investigative Dermatology, vol. 124, pp. 481-492 (2005).
Gao, J., et al., "Characterization and Antioxidant Activity of Flavonoid-Rich Extracts From Leaves of *Ampelopsis grossdentata*", Journal of Food Biochemistry, vol. 33, pp. 808-820 (2009).
Kim, J-H., et al., "Antidepressant-Like Effects of *Albizzia julibrissin* in Mice; Involvement of the 5-$HT_{1A}$ Receptor System", Pharmacology, Biochemistry and Behavior, vol. 87, pp. 41-47 (2007).
Kokila, K., et al., "Phytopharmacological Properties of *Albizia* Species: A Review", International Journal of Pharm Science, vol. 5, Suppl 4, pp. 70-73 (2013).
McCullough, J., et al., "Prevention and Treatment of Skin Aging", Ann. N.Y. Academy of Science, vol. 1067, pp. 323-331 (2006).
O'Goshi, K-I., "Suction Chamber Method for Measurement of Skin Mechanics: The Cutometer", Handbook of Non-Invasive Methods and the Skin, Second Edition, pp. 579-582, Chapter 66 (2006).
Osawa, R., et al., "Filaggrin Gene Defects and the Risk of Developing Allergic Disorders", Allergology International, vol. 60, pp. 1-9 (2011).
Rinnerthaler, M., et al., "Age-Related Changes in the Composition of the Cornified Envelope in Human Skin", Experimental Dermatology, vol. 22, pp. 329-335 (2013).
Solano, F., et al., "Hypopigmenting Agents and Updated Review on Biological, Chemical and Clinical Aspects", Pigment Cell Research, vol. 19, pp. 550-571 (2006).
Sun, H., et al., "Adjuvant-Active Fraction from *Albizia julibrissin* Saponins Improves Immune Responses by inducing Cytokine and Chemokine at the Site of Injection", International Immunopharmacology, vol. 22, pp. 346-355 (2014).
Thyssen, J., et al., "Causes of Epidermal Filaggrin Reduction and Their Role in the Pathogenesis of Atopic Dermatitis", American Academy of Allergy, Asthma & Immunology, pp. 792-799 (2014).
Zheng, X., et al., Composition and Serum Antioxidation of the Main Flavonoids from Fermented Vine Tea *Ampelopsis grossdentata*, Journal of Functional Foods, vol. 9, pp. 290-294 (2014).
Zocchi, G., "Skin-Feel Agents", Handbook of Cosmetic Science and Technology, pp. 399-419 (2001).
Database WPI, Week 200735, (Sep. 1, 2007); Thomson Scientific, London, GB; AN2007-362624, XP002761743, "Tortoise whitebait wine for health care", & CN 1 876 795 A (Liu Y) (Dec. 13, 2006) Abstract, Example 2.
Database WPI, Week 201523, (Jun. 6, 2015), Thomson Scientific, London, GB; AN 2015-18987S, XP002761744, "Radix Puerariae health tea beverage and preparation method thereof", & CN 104 305 404 A (Xu J) (Jan. 28, 2015) Abstract.
Database WPI, Week 201278, (Jul. 1, 2012), Thomson Scientific, London, GB; AN 2012-M20735, XP002761745, "A vine tea mask capsule and a method of preparing the same", & CN 102 552 092 A (Univ Fujian Agric & Forestry) (Jul. 11, 2012) Abstract.
Database WPI, Week 200468, (Sep. 24, 2004), Thomson Scientific, London, GB; AN 2004-693404, XP002761746, "Cosmetic [capable of preventing and ameliorating wrinkles]", & JP 2004 262852 A (Kanebo Ltd) (Sep. 24, 2004) Abstract.
Database WPI, Week 200764, (Aug. 16, 2007), Thomson Scientific, London, GB; AN 2007-682336, XP002761747, "Cosmetic Composition and Cosmetic for Improving Acne", & JP 2007 204414 A (Kotobuki Yasumi KK) (Aug. 16, 2007) Abstract.
Database WPI, Week 201355, (Mar. 20, 2013), Thomson Scientific, London, GB; AN 2013-K29535, XP002761748, "Antiaging sunscreen cream containing natural plant active ingredients and preparation method thereof", & CN 102 973 471 A (Univ Hanshan Normal) (Mar. 20, 2013) Abstract.
Jianhua Gao et al., "Characterization and Antioxidant Activity of Flavonoid-Rich Extracts from Leaves of Ampelopsis Grossedentata", Journal of Food Biochemistry, vol. 33, No. 6, (Dec. 1, 2009), pp. 808-820, XP055301593, US, ISSN: 0415-8884, DOI: 10.111/j.1745-4514.2009.00253.x, Abstract, Introduction experimental section: isolation and characterization of dihydromyricetine from Ampelopsis grossedentata.
Sun Hongxiang et al., "Adjuvant-active fraction from Albizia julibrissinsaponins improves immune responses by inducing cytokine and chemokine at the site of injection", International Immunopharmacology, Elsevier, Amsterdam, NL, vol. 22, No. 2, (Jul. 27, 2014), pp. 346-355, XP029060404, ISSN: 1567-1569, DOI: 10.1016/J. INTIMP.2014.07.021, Abstract, Introduction.
International Search Report for PCT/US2016/046559 dated Oct. 10, 2016.

* cited by examiner

COMPOSITIONS COMPRISING AMPELOPSIS GROSSEDENTATA AND ALBIZIA JULIBRISSIN EXTRACTS

CROSS REFERENCE TO RELATED APPLICATION

This application claims priority of the benefits of Chinese Patent Application No. 201510500612.1, filed Aug. 14, 2015, the complete disclosure of which is hereby incorporated herein by reference in its entirety.

FIELD OF THE INVENTION

The present invention relates to compositions for treating the skin barrier and improving skin hydration comprising plant extracts for use on skin. More specifically, the present invention relates to compositions comprising extracts of *Ampelopsis grossedentata* and *Albizia julibrissin* for improving the condition and appearance of the skin, such as by improving skin barrier protection, improving hydration and moisturization of the skin and reducing inflammation of the skin, and providing anti-aging properties to the skin.

BACKGROUND OF THE INVENTION

A wide variety of compositions intended for improving the appearance of skin, including improving skin hydration and moisturization, are known in art. However, most of these moisturizing agents work either through formation of occlusive films on the skin that prevent transepidermal water loss (e.g., mineral oil, petrolatum and other oils), or through humectants that attract and retain moisture on the skin surface (e. g. glycerin, propylene glycol, butylene glycol and so on). There is a need for agents that protect the skin barrier more holistically.

*Ampelopsis grossedentata* or "Moyeam" is a species of plant belonging to the Vitaceae family, genus: *Ampelopsis Michx*. The specific name *grossedentata* comes from the plant's growing structure and leaves. It is mainly distributed in middle and south of China. It also finds presence in some south-east Asian countries. Moyeam is generally grown in Zhang Jiajie, the famous mountain in Hunan province of China. The leaves and stems are used to make a herbal tea popular by the name "Moyeam" in China. The tea is very popular among health-conscious consumers for its high levels of flavonoids especially Dihydromyricetin. Traditional uses include cure for respiratory diseases, eliminating inflammation, as an anti-oxidant, regulating blood sugar and fat and as an anti-cancer agent. *Ampelopsis grossedentata* is widely used as a medicinal plant. Its dried leaves and stems, also named as Vine Tea or Mao Yan Mei, have been consumed as a health tea and herbal medicine for hundreds of years. The chemical content of this plant includes flavonoids such as dihydromyricetin and myricetin (Du, Q.; Chen, P.; Jerz, G.; Winterhalter, P. Preparative separation of flavonoid glycosides in leaves extract of *Ampelopsis grossedentata* using high-speed counter-current chromatography. J. Chromatogr. A 2004, 1040, 147-149.). It was used as folk medicine or a daily drink for the treatment of hepatitis, flu, hypertension, hyperglycemic and sore throat. (Gao, J. H.; Liu, B. G.; Ning, Z. X.; Zhao, R. X.; Zhang, A. Y.; Wu, Q. Characterization and antioxidant activity of flavonoid-rich extracts from leaves of *Ampelopsis grossedentata*. J. Food Biochem. 2009, 33, 808-820.). Modern pharmacology studies have shown that it had activities such as anticancer, liver protection, anti-oxidation, anti-inflammatory and so on (Xiao J. Zheng, Hao Xiao, Zhi Zeng, ZiW. Sun, Can Lei, Jing Z. Dong, Ying Wang. Composition and serum antioxidation of the main flavonoids from fermented vine tea (*Ampelopsis grossedentata*) has also been shown. Journal of functional foods. 2014, 9, 290-294.)

*Albizia julibrissin* is a species of tree from the Fabaceae family, native to southwestern and eastern Asia. It is known by a wide variety of common names such as "Persian silk tree" or "pink siris". It is widely planted as an ornamental plant in parks and gardens. The seeds of the plant are used as food for livestock and by wildlife. The extracts of *Albizia julibrissin* are found to have anti-depressant properties [Kim, J H; Kim, S Y; Lee, S Y; Jang, C G (2007). "Anti-depressant-like effects of *Albizzia julibrissin* in mice: Involvement of the 5-HT1A receptor system". *Pharmacology, Biochemistry, and Behavior* 87 (1): 41-7]. In traditional Chinese medicine, *Albizia julibrissin* is used to nourish the heart and calm the spirit. See http://www.acupuncture-and-chinese-medicine.com/albizza.html, accessed Jun. 15, 2015. It is also used for treating insomnia, injuries due to falls and removing carbuncles. "Shen Nong's Herbal Classic", a famous Chinese ancient book, teaches its medicinal use for mental diseases. *Albizia julibrissin* main constituents include triterpenoid saponins, lignanoids, phenolic glycosides, flavonoids, spermine macrocyclic alkaloids and so on. Among them, the triterpenoid saponins have been proved to be the main bioactive principles of this crude drug (Kokila K, Priyadharshini S D, Sujatha V. Phytopharmacological properties of *Albizia* species: a review. Int J Pharm Pharm Sci 2013; 5(Suppl. 3):70-3.). Modern pharmacology studies have shown it possessed sedative, antidepressant, anti-oxidant, anti-tumor, immunomodulatory, anti-fertility and anti-platelet activating factor receptor activities. (Hongxiang Sun, Shuwang He, Minghua Shi. Adjuvant-active fraction from *Albizia julibrissin* saponins improves immune responses by inducing cytokine and chemokine at the site of injection. International Immunopharmacology 22 (2014) 346-355).

The skin provides a vital barrier structure that protects human from environmental insults. The epidermis, where most of the skin barrier function resides, is highly stratified and has an outermost layer that is cornified. Epidermal barrier integrity disruption or dysfunction is pathologically involved in a variety of compromised skin conditions, including dry skin, skin sensitization, atopic dermatitis, psoriasis and aging. To build a strong and improved skin barrier it is necessary to increase the threshold to defend against extrinsic stimulates. Even for compromised skin conditions, the restoration of the skin barrier is also important for recovering and reducing appearance of dry, aging, inflammation and other pathological properties.

Dry skin is a common skin condition that affects almost all of people at some times in their lives. Dry skin can cause many skin problems including atopic dermatitis, eczema, psoriasis and pruritus. The moisturizing is also a key step for an elastic and transparent skin condition, which makes skin look healthy, young and beautiful.

Inflammatory skin conditions such as atopic dermatitis, eczema and sensitive skin also have a close connection with the skin's barrier properties. Epidermal integrity is necessary for the skin to defend against external stimulants.

Filaggrin is an important protein involved in skin moisturizing and immune responses through its contribution to skin barrier structure and functions. Filaggrin can be degraded to free amino acids forming a major component of natural moisturizing factor (NMF), which serves as the primary humectant of the stratum corneum (SC). 2-pyrrolidone-5-carboxylic acid (PCA) and urocanic acid (UCA) are two important NMF components, which bind water and make the surface of normal skin soft and flexible. Filaggrin, together with NMF, contribute to stratum corneum (SC) hydration and pH. Filaggrin is different from traditional moisturizing ingredients which function to increase water absorption. Filaggrin and NMF function to improve the skin barrier function and water binding capability of the epidermis. Decreased filaggrin and NMF are mainly the key factors resulting in dry skin. Restoration or improvement of filaggrin and NMF is important for healthy and lively skin. In addition, UCA may have several other functions in SC, including UV photoprotection and as a scavenger of UV-generated hydroxyl radicals [Jacob P. Thyssen and Sanja Kezic (2014) "Causes of epidermal filaggrin reduction and their role in the pathogenesis of atopic dermatitis". *J Allergy Clin Immunol* 2014; 134:792-9.].

Additionally, filaggrin is also important for the formation of the corneocyte. Filaggrin functions as an intermediate filament-associated protein (IFAP) to aggregate keratin filaments into macrofibrils, the largest filament bundles present in corneocytes. Along with several other epidermal differentiation-linked proteins, filaggrin is then cross-linked into the cornified envelope. Filaggrin contributes a strong structure that is a defense line for skin. Studies have strongly suggested that perturbation of skin barrier function as a result of reduction or complete loss of filaggrin expression leads to enhanced percutaneous transfer of allergens, further stimulation of langerhans cells which lead to Th2 immune responses. This ultimately results in the pathology of skin inflammation. Improvement of filaggrin can prevent or limit the attenuation of skin inflammation. Filaggrin is therefore in the frontline of defense, and protects the body from the entry of foreign environmental substances that can otherwise trigger aberrant immune responses [Osawa R, Akiyama M, Shimizu H (2011)"The filaggrin gene defects and the risk of developing allergic disorders." *Allergol Int.* 2011 March; 60(1):1-9.].

The function and appearance of the skin may decline with age. This decline can be caused by skin barrier dysfunction. Loricrin (LOR) is another important protein that facilitates terminal differentiation of the epidermis and formation of the skin barrier. Human LOR is an insoluble protein initially expressed in the granular layer of the epidermis during cornification and comprises 80% of the total protein mass of the cornified envelope (CE). The content of LOR reduces with age [Mark Rinnerthaler, Jutta Duschl, Peter Steinbacher, Manuel Salzmann, Johannes Bischof (2013)"Age-related changes in the composition of the cornified envelope in human skin". *Experimental Dermatology,* 2013, 22, 329-335]. It is therefore advantageous to promote the expression of LOR to reduce the effects of aging on the skin.

LOR, involucrin and filaggrin are cross-linked by the formation of e-(g-glutamyl)lysine isodipeptide bonds during epidermal differentiation. This function is catalyzed by transglutaminase 1 (TGM 1). Most TGM1 is anchored to the keratinocyte plasma membrane via fatty acyl linkages and can also function to crosslink lipids to the envelope. [Richard L Eckert, Michael T Sturniolo, Ann-Marie Broome, Monica Ruse and Ellen A Rorke (2005)"Transglutaminase Function in Epidermis" *Journal of Investigative Dermatology* (2005) 124, 481-492] Mutation or reduced amount of TGM 1 is associated with lamellar ichthyosis and other skin problems with skin barrier dysfunction. Thus an increase of TGM 1 is beneficial for improving skin strength and preventing SC from coming off.

Dry skin, aging, itching and other skin problems are related to decreased differential ability and metabolism of skin. Cell vitality is a basic source of skin physiological properties. Recovery or improvement of skin cell vitality can provide a potential differential ability and metabolism of skin, which are important for skin regeneration and defending intrinsic and extrinsic stimulate. Accordingly, it would be desirable to find active ingredients to promote filaggrin and LOR to improve skin barrier.

Applicants have surprisingly discovered that certain extracts of *Ampelopsis grossedentata* when combined with certain extracts of *Albizia julibrissin* showed unexpected synergy in providing superior skin barrier protection, reducing the signs of aging in the skin and reducing skin inflammation.

SUMMARY OF THE INVENTION

Accordingly, in one aspect, the present invention is directed to topical compositions comprising extracts of *Ampelopsis grossedentata* and *Albizia julibrissin* wherein the extracts of *Ampelopsis grossedentata* and the *Albizia julibrissin* are present in a weight ratio of 1:10 to 10:1 and a cosmetically acceptable topical carrier.

In another aspect, the present invention is directed to methods of treating skin in need of improving skin barrier function with a topical composition comprising extracts of *Ampelopsis grossedentata* and *Albizia julibrissin.*

In yet another aspect, the present invention is directed to methods of treating skin inflammation by applying to a skin in need of reducing skin inflammation a topical composition comprising extracts of *Ampelopsis grossedentata* and *Albizia julibrissin.*

In yet another aspect, the present invention is directed to methods of treating skin aging by applying to a skin in need of improving signs of aging a topical composition comprising extracts of *Ampelopsis grossedentata* and *Albizia julibrissin.*

These and other features and advantages of the present invention will be readily apparent from the following detailed description of the invention.

DETAILED DESCRIPTION OF THE INVENTION

All percentages listed herein, unless otherwise stated, are weight percentages based on the total weight of the composition.

As used herein, "skin in need of improving skin barrier function" means, without limitation, skin that is lacking in moisture, lacking in sebum, cracked, dry, itchy, scaly, xerodermic, dehydrated, skin that looks rough, peely, irritated or inflamed; skin that is painful, itchy, lacks suppleness, lacks radiance, dull or lacks lipids, has altered free fatty acids: ceramides:cholesterol ratio, has altered transepidermal water loss, has altered water barrier function, has altered skin conductance, epidermal differentiation, increased inflammation/irritation, hyperkeratinization, abnormal desquamation and bacterial proliferation, sensitive skin, compromised skin conditions like eczematic skin, skin with dermatoses such as atopic dermatosis, psoriasis, or combinations of two or more thereof.

As used herein, "skin in need of reducing skin inflammation" means a skin exhibiting redness or erythema, edema, or being reactive or sensitive to external elements. External elements include, but are not limited to, sun rays (UV, visible, IR), microorganisms, atmospheric pollutants such as ozone, exhaust pollutants, chlorine and chlorine generating compounds, cigarette smoke, cold temperature, heat, soaps and detergents, cosmetics, jewelry. Inflammatory disorders and related conditions which may be treated or prevented by use of the compositions of this invention include, but are not limited to the following: arthritis, bronchitis, contact dermatitis, atopic dermatitis, psoriasis, seborrheic dermatitis, sumac and poison oak dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, post-inflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, poison oak, poison sumac, insect bites, folliculitus, alopecia, and secondary conditions and the like.

As used herein, "skin in need of improving or reducing the signs of aging" means a skin that is, but not limited to, sagging, loose, lax, rough, wrinkly, thinned, and uneven. Improving the signs of aging means improving the firmness of the skin, improving the texture of the skin, improving the appearance of wrinkles in skin, improving the skin tone or the treatment of external aggressions in skin.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook of Non-Invasive Methods and the Skin, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle and fine line formation in skin.

As used herein, "treatment of external aggressions in skin" means the reduction or prevention of the damage from external aggressions in skin. Examples of external aggressions include, but are not limited to, damage to the skin from the use of cleansers (e.g., topical cleansers containing surfactants), make-up, shaving as well as environmental damage such as from UV light (e.g., sun damage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "improving the skin tone" means the lightening of the appearance of the skin (e.g., lightening pigmented marks or lesions, reducing skin sallowness, and/or evening the color of the skin).

As used herein, "cosmetically/dermatologically acceptable" means suitable for use in contact with tissues (e.g., the skin or hair) without undue toxicity, incompatibility, instability, irritation, allergic response, and the like.

As used herein, the term "safe and effective amount" means an amount sufficient to induce the desired effect, but low enough to avoid serious side effects. The safe and effective amount of the compound, extract, or composition will vary with, e.g., the age, health and environmental exposure of the end user, the duration and nature of the treatment, the specific extract, ingredient, or composition employed, the particular pharmaceutically-acceptable carrier utilized, and like factors.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As described herein, applicants have discovered that compositions comprising extracts of *Ampelopsis grossedentata* and *Albizia julibrissin* provide unexpectedly good skin barrier function, and reduce, inhibit, treat, and delay any signs of skin barrier function impairment. In particular, applicants have discovered that extracts of *Ampelopsis grossedentata* and *Albizia julibrissin* induce promotion of natural moisturizing factors by the skin itself, and such induced production of natural moisturizing factors will have a beneficial effect in improving skin barrier function and skin hydration and moisturization.

According to one aspect of the present invention, compositions comprising extracts of and extracts of the flowers of *Albizia julibrissin* when combined in a weight ratio of 1:10 to 10:1 provide a significant increase in the natural moisturizing factors of the skin of a human being.

*Ampelopsis grossedentata* extract: Any suitable manner of preparing the extracts of *Ampelopsis grossedentata* for use in accordance with the present invention may be used. Suitable extracts may be obtained using conventional methods including, but not limited to, direct extraction from the biomass by grinding, macerating, pressing, squeezing, mashing, centrifuging, and/or processes such as cold percolation, agitation/distillation, microwave assisted extraction, sonication, supercritical/subcritical $CO_2$ compressed gas extraction with or without polarity modifier, pressurized solvent extraction, accelerated solvent extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. In particular, an extract in accordance with the present invention preferably is a solvent-based extraction made by grinding or macerating plant material in a solvent, typically an organic solvent such as an alcohol, acetone, liquid carbon dioxide with or without polarity modifier, hexane, or chloroform. The resulting extract comprised mainly non-polar compounds. The plant biomass preferably is separated entirely from the extraction, and is not used after extraction.

Any of a variety of solvents including polar solvents, non-polar solvents, or combinations of two or more thereof may be used in methods of comprising solvent extraction. Preferably, polar solvents are used. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In certain preferred embodiments, the extract is a polar extract. Polar extract means the extract is produced by subjecting the plant or parts of the plant to a polar solvent. In a certain embodiment, the extract is prepared by pulverizing the leaves of *Ampelopsis grossedentata* and extracting using a polar solvent having a dielectric constant value of between 1 and 100 at 20° C., preferably a dielectric constant of a value between 4 and 60 at 20° C., more preferably a dielectric constant of a value between 4 and 50 at 20° C., and even more preferably a dielectric constant of a value between 4 and 40 at 20° C. Examples of preferred polar solvents include $C_1$-$C_8$ alcohols, $C_1$-$C_8$ polyols/glycols, $C_1$-$C_8$ organic acids, water and combinations of two or more thereof having a dielectric constant value of between 1 and 100, preferably between 4 and 60, and more preferably between 5 and 40 at 20° C., including, but not limited to, those solvents and combinations of solvents having the desired dielectric constant value as disclosed in "Dielectric Constants of Some Organic Solvent-Water Mixtures at Various Temperatures," Akerlof, Gosta; *JACS*, Vol. 54, No. 11 (November 1932), pp. 4125-4139, incorporated herein by reference. In certain preferred embodiments, the polar extract is extracted using one or more $C_1$-$C_8$ alcohols, $C_1$-$C_8$ polyols, $C_1$-$C_8$ glycols, and combinations of two or more thereof. In certain more preferred embodiments, the extract is extracted using one or more $C_1$-$C_4$ alcohols, $C_1$-$C_4$ polyols, and/or $C_1$-$C_4$ glycols. In certain more preferred embodiments, the extract is prepared using a solvent comprising methanol, ethanol, or a combination thereof with or without presence of water. In certain preferred embodiments, the extract may be further refined by charcoal (also referred to as active carbon) treatment.

In certain preferred embodiments, the extract of the invention is an extract prepared by pulverizing the *Ampelopsis grossedentata* leaves and extracting using a solvent having a dielectric constant of a value between about 1 and about 80 at 20° C., preferably a dielectric constant of a value between about 2 and about 60 at 20° C., more preferably a dielectric constant of a value between about 2 and about 40 at 20° C., and even more preferably a dielectric constant of a value between about 2 and 35 at 20° C.

In certain embodiments, the composition may additionally include extracts from other parts of an *Ampelopsis grossedentata* plant for example, one or more of the stem, bark, roots, fruits, seeds, or flowers. In other embodiments, the composition is essentially free from extracts of other non-leaf parts of *Ampelopsis grossedentata* plant.

In certain embodiments, the composition may comprise extracts from cell cultures of plants of *Ampelopsis grossedentata*.

Any suitable amount of *Ampelopsis grossedentata* extract may be used in the topical compositions of the present invention. In certain preferred embodiments, the compositions comprise from greater than zero to about 20% *Ampelopsis grossedentata* extract. In certain other preferred embodiments, the compositions comprise from about 0.0001 to about 20%, from about 0.001 to about 10%, from about 0.01 to about 5%, from about 0.1 to about 5%, or from about 0.2 to about 2% *Ampelopsis grossedentata* extract. In certain other preferred embodiments, the compositions comprise from greater than zero to about 1%, from about 0.0001 to about 1%, from about 0.001 to about 1%, or from about 0.01 to about 1% *Ampelopsis grossedentata* extract. In certain other preferred embodiments, the compositions comprise from about 1 to about 5%, preferably from about 2 to about 5% *Ampelopsis grossedentata* extract. In certain preferred embodiments, the amounts of the *Ampelopsis grossedentata* extract are from the leaf of *Ampelopsis grossedentata*.

*Albizia julibrissin* extract: Any suitable manner of preparing the extracts of *Albizia julibrissin* for use in accordance with the present invention may be used. Suitable extracts may be obtained using conventional methods including, but not limited to, direct extraction from the biomass by grinding, macerating, pressing, squeezing, mashing, centrifuging, and/or processes such as cold percolation, agitation/distillation, microwave assisted extraction, sonication, supercritical/subcritical $CO_2$ compressed gas extraction with or without polarity modifier, pressurized solvent extraction, accelerated solvent extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. In particular, an extract in accordance with the present invention preferably is a solvent-based extraction made by grinding or macerating plant material in a solvent, typically an organic solvent such as an alcohol, acetone, liquid carbon dioxide with or without polarity modifier, hexane, or chloroform. The resulting extract comprised mainly non-polar compounds. The plant biomass preferably is separated entirely from the extraction, and is not used after extraction.

Any of a variety of solvents including polar solvents, non-polar solvents, or combinations of two or more thereof may be used in methods of comprising solvent extraction. Preferably, polar solvents are used. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In certain preferred embodiments, the extract is a polar extract. Polar extract means the extract is produced by subjecting the plant or parts of the plant to a polar solvent. In a certain embodiment, the extract is prepared by pulverizing the flowers of *Albizia julibrissin* and extracting using a polar solvent having a dielectric constant value of between 1 and 100 at 20° C., preferably a dielectric constant of a value between 4 and 60 at 20° C., more preferably a dielectric constant of a value between 4 and 50 at 20° C., and even more preferably a dielectric constant of a value between 4 and 40 at 20° C. Examples of preferred polar solvents include $C_1$-$C_8$ alcohols, $C_1$-$C_8$ polyols/glycols, $C_1$-$C_8$ organic acids, water and combinations of two or more thereof having a dielectric constant value of between 1 and 100, preferably between 4 and 60, and more preferably between 5 and 40 at 20° C., including, but not limited to, those solvents and combinations of solvents having the desired dielectric constant value as disclosed in "Dielectric Constants of Some Organic Solvent-Water Mixtures at Various Temperatures," Akerlof, Gosta; *JACS*, Vol. 54, No. 11 (November 1932), pp. 4125-4139, incorporated herein by reference. In certain preferred embodiments, the polar extract is extracted using one or more $C_1$-$C_8$ alcohols, $C_1$-$C_8$ polyols, $C_1$-$C_8$ glycols, and combinations of two or more thereof. In certain more preferred embodiments, the extract is extracted using one or more $C_1$-$C_4$ alcohols, $C_1$-$C_4$ polyols, and/or $C_1$-$C_4$ glycols. In certain more preferred embodiments, the extract is prepared using a solvent comprising methanol, ethanol, or a combination thereof with or without presence of water. In certain preferred embodiments, the extract may be further refined by charcoal (also referred to as active carbon) treatment.

In certain preferred embodiments, the extract of the invention is an extract prepared by pulverizing the *Albizia julibrissin* flowers and extracting using a solvent having a dielectric constant of a value between about 1 and about 80 at 20° C., preferably a dielectric constant of a value between about 2 and about 60 at 20° C., more preferably a dielectric constant of a value between about 2 and about 40 at 20° C., and even more preferably a dielectric constant of a value between about 2 and 35 at 20° C.

In certain embodiments, the composition may additionally include extracts from other parts of an *Albizia julibrissin* tree for example, one or more of the stem, bark, wood, roots, leaves, fruits, or seeds. In other embodiments, the composition is essentially free from extracts of other non-flower parts of *Albizia julibrissin* tree.

In certain embodiments, the composition may comprise extracts from cell cultures of trees of *Albizia julibrissin*.

Any suitable amount of *Albizia julibrissin* extract may be used in the topical compositions of the present invention. In certain preferred embodiments, the compositions comprise from greater than zero to about 20% *Albizia julibrissin* extract. In certain other preferred embodiments, the compositions comprise from about 0.0001 to about 20%, from about 0.001 to about 10%, from about 0.01 to about 5%, from about 0.1 to about 5%, or from about 0.2 to about 2% *Albizia julibrissin* extract. In certain other preferred embodiments, the compositions comprise from greater than zero to about 1%, from about 0.0001 to about 1%, from about 0.001 to about 1%, or from about 0.01 to about 1% *Albizia julibrissin* extract. In certain other preferred embodiments, the compositions comprise from about 1 to about 5%, preferably from about 2 to about 5% *Albizia julibrissin* extract. In certain preferred embodiments, the amounts of the *Albizia julibrissin* extract are from the flower of *Albizia julibrissin*.

When the topical compositions containing the extracts according to the present invention are applied to the skin it is believed only a certain percentage of the extracts according to the present invention penetrates the epidermis. The penetration percentage is determined by a lot of factors, such as molecule weight, solubility etc, with very broad variation. The present invention further comprises a method of improving the barrier function and improving hydration and moisturization of the skin by applying to skin in need of improving skin barrier function and improving skin moisturization a composition comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1. The method comprises for example topically applying a composition of the present invention comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1, to skin in need of improving skin barrier function. Such topical application may be to any skin in need of treatment on the body, for example skin of the face, lips, neck, chest, back, arms, buttocks, axilla, and/or legs. Preferably, the extracts are polar extracts of *Ampelopsis grossedentata* and *Albizia julibrissin*.

The present invention further comprises a method of reducing skin dryness by applying to skin in need a composition comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1. The method comprises for example topically applying a composition of the present invention comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1, to skin in need of reducing skin inflammation. Such topical application may be to any skin in need of treatment on the body, for example skin of the face, lips, neck, chest, back, buttocks, arms, axilla, and/or legs. Preferably, the extracts are polar extracts of *Ampelopsis grossedentata* and *Albizia julibrissin*.

The present invention further comprises a method of reducing skin inflammation by applying to skin in need of reducing skin inflammation a composition comprising extracts of *Ampelopsis grossedentata* and *Albizia julibrissin* in an inflammation-reducing therapeutically effect amount. In particular, the method uses a combination of extracts of *Ampelopsis grossedentata* leaves and *Albizia julibrissin* flowers in a weight ratio ranging from 1:10 to 10:1. The method comprises for example topically applying a composition of the present invention comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1, to skin in need of reducing skin inflammation. Such topical application may be to any skin in need of treatment on the body, for example skin of the face, lips, neck, chest, back, buttocks, arms, axilla, and/or legs. Preferably, the extracts are polar extracts of *Ampelopsis grossedentata* and *Albizia julibrissin*.

The present invention further comprises a method of improving skin aging by applying to skin in need of improving skin aging a composition comprising extracts of *Ampelopsis grossedentata* and *Albizia julibrissin* in a therapeutically effective amount for reducing a sign of aging. In particular the method uses a combination of extracts of *Ampelopsis grossedentata* leaves and *Albizia julibrissin* flowers in a weight ratio ranging from 1:10 to 10:1. The method comprises for example topically applying a composition of the present invention comprising extracts of *Ampelopsis grossedentata* and *Albizia julibrissin*, in particular a combination of extracts of *Ampelopsis grossedentata* leaves and *Albizia julibrissin* flowers in a weight ratio ranging from 1:10 to 10:1, to skin in need of improving skin aging. Such topical application may be to any skin in need of treatment on the body, for example skin of the face, lips, neck, chest, back, buttocks, arms, axilla, and/or legs. Preferably, the extracts are polar extracts of *Ampelopsis grossedentata* and *Albizia julibrissin*.

Any suitable amount of extracts of *Ampelopsis grossedentata* and *Albizia julibrissin* may be used in the compositions of the present invention. Preferably, the compositions comprise a safe and effective amounts of extracts of *Ampelopsis grossedentata* and *Albizia julibrissin*. In particular, the amounts of the extracts of *Ampelopsis grossedentata* and *Albizia julibrissin* to be used preferably is selected to achieve the desired treatment of a given skin condition. The extract of *Ampelopsis grossedentata* and the extract of *Albizia julibrissin* are present in the extract composition in amounts from a weight ratio, by weight of the extract composition of about 1:10 to about 10:1, preferably from about 1:7 to about 7:1, more preferably from about 1:5 to about 5:1, even more preferably from about 1:3 to about 3:1 and even more preferably from about a ratio of 1:1.

Any suitable carrier may be used in the compositions. Preferably, the carrier is a cosmetically-acceptable carrier. As will be recognized by those of skill in the art, cosmetically acceptable carriers comprise carriers that are suitable for use in contact with the body, in particular the skin, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 98% to about 99.8% by weight of the composition.

The carrier can be in a wide variety of forms. For example, carriers in the form of emulsions, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps using a Brookfield RVT viscometer.

Examples of suitable cosmetically-acceptable carriers include cosmetically acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, micro-needle patches, bandages, hydrogels, film-forming products, facial and skin masks, make-up, liquid drops, and the like. These product types may contain several types of cosmetically-acceptable carriers including, but not limited to solutions, suspensions, emulsions such as micro-emulsions and nano-emulsions, gels, solids, liposomes, other encapsulation technologies and the like.

The following are non-limiting examples of carriers. Other carriers can be formulated by those of ordinary skill in the art. In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and non-ionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99% of solvent.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid 10 hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type, and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers, and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid, or dissolvable substrate (e.g., a wipe, mask, pad, glove, or strip).

The compositions of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, antimicrobial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH changing agents, and the like.

Examples of various suitable additional cosmetically acceptable actives include hydroxy acids; benzoyl peroxide; D-panthenol; UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide; carotenoids; free radical scavengers; spin traps; retinoids and retinoid precursors such as 30 retinol, retinoic acid and retinyl palmitate; ceramides; polyunsaturated fatty acids; essential fatty acids; enzymes; enzyme inhibitors; minerals; hormones such as estrogens; steroids such as hydrocortisone; 2-dimethylaminoethanol; copper salts such as copper chloride; peptides containing copper such as Cu:Gly-His-Lys, coenzyme Q10; amino acids such a proline; vitamins; lactobionic acid; acetyl-coenzyme A; niacin; riboflavin; thiamin; ribose; electron transporters such as NADH and FADH2; and other botanical extracts such as oat, aloe vera, Feverfew, Soy, Shiitake mushroom extracts, and derivatives and mixtures thereof.

In certain preferred embodiments, the skin care compositions comprise extracts of *Ampelopsis grossedentata* and *Albizia julibrissin*, and at least one additional skin moisturizing active agent. Examples of additional skin moisturizing agents include glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, or mixtures thereof In certain preferred embodiments, the compositions of the present invention are skin care compositions that comprise extracts of *Ampelopsis grossedentata* and *Albizia julibrissin* and at least one additional agent for improving the signs of aging. Examples of suitable additional agents improving the signs of aging include, but are not limited to, tropoelastin promoters, collagen promoters, retinoids, hyaluronic acid, dimethylaminoethanol, N,N,N',N'-Tetrakis(2-hydroxypropyl)ethylenediamine, alpha hydrox acids, polyhydroxyacids, and combinations of two or more thereof.

"Tropoelastin promoters," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Examples of suitable tropoelastin promoters include, but are not limited to, blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copperzinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, *cotinus* extracts, feverfew extracts, and combinations thereof. In a particularly preferred embodiment, the tropoelastin promoter is selected from blackberry extracts, feverfew extracts, and combinations thereof.

By "cotinus extract," it is meant an extract of the leaves of "*Cotinus coggygria*," such as a water extract thereof, available from Bilkokoop of Sofia, Bulgaria.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract. One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name "SymMatrix."

Extracts of "*Phyllanthus niruri*" may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev. Preferably, a low molecular weight fraction of *Phyllanthus niruri* is used, for instance a fraction of *Phyllanthus niruri* substantially free of molecular species having a molecular weight of greater than about 100,000 daltons. Preferably, such low molecular weight fraction is water extractable from the *Phyllanthus niruri* plant.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters" according to the present invention include all natural or synthetic compounds that are not retinoids, or derived from retinoids, and are capable of enhancing the production of collagen in the human body.

Examples of suitable collagen promoters include, but are not limited to the following: Retinoids including retinol, retinaldehyde, and retinoic acid, extracts of feverfew (*Tanacetum parthenium*), extracts of *Centella asiatica*, and extracts of *Siegesbeckia orientalis*; extracts of soy; collagen-promoting peptides; ursolic acid; and asiaticoside.

*Centella asiatica*, also known as Violette marronne on Reunion Island, Gotu Kola or Indian pennywort in India, *Centella repanda* in North America, and Talapetraka in Madagascar, is a polymorphous herb and belongs to the family of Umbelliferae (Apiaceae), particularly to the Hydrocotyle subfamily. It grows wild throughout the tropics and prefers moist and shady regions at an altitude of about 600 to 1200 meters above sea level. *Centella asiatica* has three varieties: *Typica, Abyssinica*, and *Floridana*. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following matrikine peptides, (i.e., a peptide derived from the degradation of extracellular matrix proteins—collagen, elastin, or proteoglycan) including palmitoyl pentapeptides, in particular Pal-Lys-Thr-Thr-Lys-Ser-OH, available as MATRIXYL from Sederma (Croda International Group of Edison, N.J.); GHK copper peptide available as PROCYTE from Photomedex of Montgomeryville, Pa.; Palmitoyl GHK peptide available as Biopoeptide CL from Sederma (Croda International Group of Edison, N.J.); Biomimetic tetrapeptides, such as those available as Chronoline Tri Peptide from Unipex of Québec, Canada; and Palmitoyl tri-peptide, available as Syn-Coll from DSM of Basel, Switzerland.

Ursolic acid is also known as pentacyclic triterpene acid, Prunol, Malol, Urson, betaursolic acid and 3-Beta-Hydroxy-Urs-12-En-28-Oic Acid. It is commercially available for example from Sigma-Aldrich of St. Louis, Mo.

Asiaticoside, also known chemically as: [6-[[3,4-dihydroxy-6-(hydroxymethyl)-5-(3,4,5-trihydroxy-6-methyl-oxan-2-yl)oxyoxan-2-yl]oxymethyl]-3,4,5-trihydroxyoxan-2-yl]10,11-dihydroxy-9-(hydroxymethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Santé Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

The compositions of the present invention may further comprise at least one skin lightening active agent. Examples of suitable skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea Coposita* root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliants include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), isotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

Compositions of the present invention may include a cosmetically effective amount of one or more anti-inflammatory compounds. Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following: *Phellodendron amurense* Cortex Extract (PCE), Non-Denatured Soy (*Glycine max*), Feverfew (*Tanacetum parthenium*), Ginger (*Zingiber officinale*), Ginko (*Ginkgo biloba*), Madecassoside (*Centella asiatica* extract ingredient), *Cotinus* (*Cotinus coggygria*), Butterbur Extract (*Petasites hybridus*), Goji Berry (*Lycium barbarum*), Milk Thistle Extract (*Silybum marianum*), Honeysuckle (*Lonicera japonica*), Basalm of Peru (*Myroxylon pereirae*), Sage (*Salvia officinalis*), Cranberry Extract (*Vaccinium oxycoccos*), Amaranth Oil (*Amaranthus cruentus*), Pomegranate (*Punica granatum*), Yerbe Mate (*Ilex paraguariensis* Leaf Extract), White Lily Flower Extract (*Lilium candidum*), Olive Leaf Extract (*Olea europaea*), Phloretin (apple extract), Oat Flour (*Aveena sativa*), Lifenol (Hops: *Humulus lupulus*) Extract, Bugrane P (*Ononis spinosa*), Licochalcone (Licorice: *Glycyrrhiza* inflate extract ingredient), Symrelief (Bisabolol and Ginger extract), combinations of two or more thereof, and the like.

In one embodiment, the anti-inflammatory agent is a resorcinol. Particularly suitable substituted resorcinols include 4-hexyl resorcinol and 4-octylresorcinol, particularly 4-hexyl resorcinol. 4-Hexyl resorcinol is commercially available as "SYNOVEA HR" from Sytheon of Lincoln Park, N.J. 4-Octylresorcinol is commercially available from City Chemical LLC of West Haven, Conn.

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

A variety of other materials may also be present in the compositions of the present invention. In certain preferred embodiments, the composition comprises one or more topical ingredients selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β,β-trehalose, α,β-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc., New York, N.Y.) and include, but are not limited to anionic surfactants such as sulfates, cationic surfactants such as betaines, amphoteric surfactants such as sodium coco glycinate, noionic surfactants such as alkyl polyglucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name, "Versene 100XL."

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of conditioners which impart additional attributes, such as gloss to the hair, are suitable for use in this invention. Examples include, but are not limited to, volatile silicone conditioning agent having an atmospheric pressure boiling point less than about 220° C. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable conditioners include cationic polymers, including polyquarterniums, cationic guar, and the like.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

Any fragrance compositions suitable for use on skin may be used in the composition according to the present invention.

In certain preferred embodiments, the present invention is in the form of a substrate comprising a composition of the present invention. Any suitable substrate may be used. Examples of suitable substrates and substrate materials are disclosed, for example, in U.S. Pat. No. 7,452,547 and US2009/0241242 which are incorporated herein by reference in their entirety.

In certain preferred embodiments, the substrate is a wipe, glove, or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval. For certain embodiments, the substrate is a glove such as described in U.S. Published Application No 2006/0141014 which is incorporated herein in its entirety. In one embodiment of the invention, the product includes a plurality of water-insoluble substrates of different shapes.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like. The composition may be applied in a variety of manners or forms, including, without limitation, as a leave-on cream, mask, and/or serum.

In further additional embodiments, the methods of the present invention comprise applying at least two different compositions or products comprising the extracts of *Ampelopsis grossedentata* and *Albizia julibrissin* to the skin. For example, the methods may comprise applying a first composition comprising the extracts of *Ampelopsis grossedentata* and *Albizia julibrissin* to skin in need of improving skin barrier function and improving skin hydration and moisturization, followed by applying a second composition comprising the extracts of *Ampelopsis grossedentata* and *Albizia julibrissin*, that is different from the first composition, to the skin in need of treatment. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum, and the other is a facial mask or wipe. In certain other preferred embodiments, at least one of the first and second compositions is a cleanser and the other is a lotion or cream.

While the foregoing description represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description. It will be appreciated that in the claims, the term "comprises/comprising" does not exclude the presence of other elements or steps. In addition, singular references do not exclude a plurality. The terms "a", "an", "first", "second", etc., do not preclude a plurality.

EXAMPLES

The following test methods were used in the Examples.

Assay 1: In Vitro Filaggrin Protein Assay

Skin epidermal equivalents from EpiKutis system (Shaanxi BioCell Biotechnology Co. Ltd., China) were used for the following tests. 3-D skin equivalent Epikutis system consists of normal, human-derived epidermal keratinocytes which have been cultured to form a highly differentiated model of the human epidermis. BioCell's Epikutis skin equivalent models, each 8 mm in diameter were used in the following test.

The test materials (actives) were prepared as below:

This example illustrates the making of a culture medium with 0.001% extract. The crude extract was first diluted with DMSO (dimethyl sulfoxide) as a 10% solution. Then the diluted extract was added to the cell culture media. Additional DMSO was added so that the concentration of the extract in the cell culture media was 0.001% by weight and the amount of DMSO was 0.1% in the cell culture media.

The blank control medium in the test was culture medium containing 0.1% DMSO.

Upon receipt, epidermal equivalents were incubated for 24 h at 37° C. in maintenance medium. After incubation, the equivalents were treated with culture medium containing plant extracts or a blank control medium for another 24 h at 37° C.

3 epidermal equivalents were repeated in every test group.

Sections of the skin epidermal equivalents (5 µm in thickness) were cut using a cryostat (Leica CM3050s) and fixed with acetone for 10 min at −20° C. Filaggrin was detected by incubating tissue sections with mouse monoclonal antibodies directed against filaggrin (1/100, Abcam, Cambridge, UK) for 2 h. Staining and visualization were performed by the streptavidin/peroxidase method using the LSAB+System-HRP with a DAKO Autostainer (Dako) in accordance with the manufacturer's instructions for use. As a control of non-specific labelling, the primary antibody was omitted. Multiple sections of each specimen were processed to ensure representative samples. To evaluate protein localization, a confocal laser-scanning microscope (OLYMPUS-BX53) was utilized. Result of IOD (Integral Optical Density) was quantitatively analyzed with IPP software (Image-Pro Plus from Media Cybernetics, US) as the quantity of filaggrin protein. The filaggrin promotion over blank control was calculated by the following formula:

The filaggrin promotion over blank control=(IOD value of specific sample−IOD value of blank control)/IOD value of blank control×100%

Statistical difference between the blank controls and experimental groups was determined by use of two-tailed and equal variance hypothesis student T-test and a p-value less than 0.05 was considered as significant difference.

Assay 2: In Vitro Sodium L-pyrrolidone Carboxylate (PCA) Assay

The test sample was prepared using the method given in Assay 1. The skin epidermal equivalents were treated with the culture medium containing plant extracts or blank control medium as described in the assay 1 for further PCA assay. 3 epidermal equivalents were repeated in every test group.

The skin epidermal equivalents were extracted with 500 µl deionized water by ultrasonic wave for 30 mins. Every epidermal equivalent was extracted twice. The extract was centrifuged at 14000 rpm for 10 mins. 4 µL acetonitrile and 8 µL 1M ammonium formate were added into 388 µL supernatant. PCA was analyzed by RP-HPLC using a RP-18 silicagel column, mobile phase of 20 mM ammonium formate and 1% acetonitrile, pH 7.8, flow rate 1 mL/min. PCA was tested as PCA quantity per equivalence. The PCA promotion over blank control was calculated by the following formula:

The PCA promotion over blank control=(the PCA quantity per equivalent of a specific sample−the PCA quantity per equivalent of blank control)/ the PCA quantity per equivalent of blank control×100%.

Statistical difference between the blank controls and experimental groups was determined by use of two-tailed and equal variance hypothesis student T-test and a p-value less than 0.05 was considered as significant difference.

Assay 3: In Vitro Transglutaminase-1 (TGM1) Protein Assay

The test sample was prepared using the method given in Assay 1. The skin epidermal equivalents were treated with culture medium containing plant extracts or blank control medium as described in the assay 1 for further TGM1 protein assay. 3 epidermal equivalents were repeated in every test group.

Sections of the skin epidermal equivalents, 5 µm in thickness, were cut using a cryostat (Leica CM3050s) and fixed with acetone for 10 min at −20° C. Transgluminase-1 was detected by incubating tissue sections with mouse monoclonal antibodies directed against transgluminase-1 (1/800, Abcam, Cambridge, UK) for 2 h. Staining and visualization were performed by the streptavidin/peroxidase method using the LSAB+System-HRP with a DAKO Autostainer (Dako) in accordance with the manufacturer's instructions for use. As a control of non-specific labelling, the primary antibody was omitted. Multiple sections of each specimen were processed to ensure representative samples. To evaluate protein localization, a confocal laser-scanning microscope (OLYMPUS-BX53) was utilized. Result of IOD (Integral Optical Density) was quantitatively analyzed with IPP software as the quantity of TGM1 protein. The TGM1 promotion over blank control was calculated by the following formula:

The TGM1 promotion over blank control=(IOD value of specific sample−IOD value of blank control)/IOD value of blank control×100%

Statistical difference between the blank controls and experimental groups was determined by use of two-tailed and equal variance hypothesis student T-test and a p-value less than 0.05 was considered as significant difference.

Assay 4: MTT Skin Equivalent Growth State Evaluation—Skin Metabolic Activity Assay The growth state of a skin equivalent is related to the potential quality of epidermis and skin barrier to be built up. The skin metabolic activity is reflected in the growth state of a skin equivalent. This was evaluated using the MTT assay described as follows.

The test sample was prepared using the method given in Assay 1. The skin epidermal equivalents were treated with culture medium containing plant extracts or blank control medium as described in the assay 1 for further MTT assay.

3 epidermal equivalents were repeated in every test group.

The MTT Assay is a colorimetric assay system that measures the reduction of a yellow Methylthiazolyldiphenyl-tetrazolium bromide (MTT) into an insoluble purple product by the mitochondria of viable cells.

The skin epidermal equivalents were treated with MTT (3-(4,5-cimethylthiazol-2-yl)-2,5-diphenyl tetrazolium bromide, sigma) for 3 hours, followed by washing 3 times using Dulbecco's Phosphate Buffered Saline (DPBS). Then the equivalents were transferred to a new chamber and incubated with isopropanol over night at 4° C. After being dissolved, the tissues were impaled to further release lysates. The lysates were measured at a wavelength of 570 nm using isopropanol as the solvent control.

The skin metabolic activity was calculated by the following formula:

Skin metabolic activity rate (%)=(OD value of specific sample concentration−OD value of control without DMSO)/(OD value of blank control group−OD value of control without DMSO)× 100. (OD: optical density).

And the promotion of skin metabolic activity over blank control was calculated by the following formula, The promotion of skin metabolic activity over blank control=skin metabolic activity rate of specific sample (%)−skin metabolic activity rate of blank control (%).

Statistical difference between the blank controls and experimental groups was determined by use of two-tailed and equal variance hypothesis student T-test and a p-value less than 0.05 was considered as significant difference.

Assay 5: In Vitro Loricrin (LOR) Protein Assay

The test sample was prepared using the method given in Assay 1. The skin epidermal equivalents were treated with culture medium containing plant extracts or blank control medium as described in the assay 1 for further LOR protein assay.

3 epidermal equivalents were repeated in every test group.

Sections of the skin epidermal equivalents, 5 μm in thickness, were cut using a cryostat (Leica CM3050s) and fixed with acetone for 10 min at −20° C. Loricrin was detected by incubating tissue sections with mouse monoclonal antibodies directed against loricrin (1/250, Abcam, Cambridge, UK) for 2 h. Staining and visualization were performed by the streptavidin/peroxidase method using the LSAB+System-HRP with a DAKO Autostainer (Dako) in accordance with the manufacturer's instructions for use. As a control of non-specific labelling, the primary antibody was omitted. Multiple sections of each specimen were processed to ensure representative samples. To evaluate protein localization, a confocal laser-scanning microscope (OLYMPUS-BX53) was utilized. Result of IOD (Integral Optical Density) was quantitatively analyzed with IPP software as the quantity of LOR protein. The LOR promotion over blank control was calculated by the following formula:

The LOR promotion over blank control=(IOD value of specific sample−IOD value of blank control)/ IOD value of blank control×100%

Statistical difference between the blank controls and experimental groups was determined by use of two-tailed and equal variance hypothesis student T-test and a p-value less than 0.05 was considered as significant difference.

Assay 6: Skin Barrier Quality Evaluation with Penetration Assay of SLS

Skin with high quality skin barrier can effectively block the penetration of external harmful material into the skin and cause the reduction of skin metabolic activity. A higher skin metabolic activity mean less penetration of harmful material and further shows skin with a higher skin barrier function.

In this study we used Sodium Lauryl Sulfate (SLS) as the harmful material.

The test sample was prepared using the method given in Assay 1. The skin epidermal equivalents were treated with culture medium containing plant extracts or blank control medium as described in the assay 1 for further skin metabolic activity assay.

3 epidermal equivalents were repeated in every test group.

After being transferred to a 6-wells plate, the equivalents were topically treated with 1% Triton X-100 (Sodium Lauryl Sulfate, Sigma) and culturing for 3 h or 6 h at 37±1° C., 5±1% $CO_2$, 95% Hm. The samples were then washed 15 times with DPBS.

The epidermal equivalents were treated with MTT (3-(4,5-cimethylthiazol-2-yl)-2,5-diphenyl tetrazolium bromide, Sigma) for 3 h. This was followed by washing the equivalents 3 times using Dulbecco's Phosphate Buffered Saline (DPBS), and then transferring to a new chamber and incubating with isopropanol over night at 4° C. After being dissolved, the tissues were impaled to further release lysates. The lysates were measured at a wavelength of 570 nm using isopropanol as the solvent control.

The skin metabolic activity rate reflects the penetration of SLS and skin barrier function. The skin metabolic activity was calculated by the following formula:

Skin metabolic activity rate (%)=(OD value of specific sample concentration−OD value of control without DMSO)/(OD value of blank control group−OD value of control without DMSO)× 100. (OD: optical density).

Statistical difference between the blank controls and experimental groups was determined by use of two-tailed and equal variance hypothesis student T-test and a p-value less than 0.05 was considered as significant difference.

Assay 7: Gene Expression Study

The test sample was prepared using the method given in Assay 1.

Human keratinocytes were inoculated in 6-well culture plates, maintained at 37° C., 5% CO2. When 40% confluence was achieved, the keratinocytes were incubated with culture medium containing plant extracts or blank control medium (culture medium containing 0.1% DMSO) for 24 h at 37° C., 5% CO2. After 24 h of incubation, total RNA was extracted with TRIzol®reagent (Life Science) and reversely transcribed using PrimeScript®RT reagent Kit Perfect Real Time (TaKaRa). The primers in the study were from Takara (Dalian, Conn.), including LOR (Genbank number NM-00427), TGM1 (Genbank number: NM_00359.2), FLG (Genbank number: NM_002016) and Caspase-14 (Genbank number: NM_012114.2). Quantitative RT-PCR was performed using SYBR Green Real time PCR Master Mix (TaKaRa). The reaction was performed in CFX96 Detection System (BIO-RAD). The gene expression result was analyzed by using real-time quantitative PCR and the method of $2^{-\Delta\Delta Ct}$.

The promotion of gene expression vs blank control was calculated using the following formula:

> The promotion of gene expression vs blank control (%)=(the gene expression of specific sample–gene expression of blank control)/gene expression of blank control×100%.

Statistical difference between the blank controls and experimental groups was determined by use of two-tailed and equal variance hypothesis student T-test and a p-value less than 0.05 was considered as significant difference.

Assay 8: Collagen Generation Assay

Collagen is the most abundant connective material within the dermis, which is a fibrous protein whose primary function is to maintain skin firmness. With age, the amount of collagen in the skin decreases [C. Castelo-Branco, M. Duran, J. Gonzilez-Merlo (1992)"Skin collagen changes related to age and hormone replacement therapy" Maturitas (1992) October; 15(2):113-9.] Exogenous aging induced by UV, smoke, pollution and lifestyle also leads to goes with collagen degradation [L Baumann (2007)"Skin ageing and its treatment" Journal of Pathology (2007); 211: 241-251] [Jerry L. Mccullough and Kristen M. Kelly (2006) "Prevention and Treatment of Skin Aging" Ann. N.Y. Acad. Sci. (2006) 1067: 323-331.]

T-75 cm$^2$ flasks of human fibroblast were washed twice in PBS, placed on ice and 2 ml of cold RIPA Lysis Buffer was added (Beyotime, Conn.). Cells were collected by scraping and the supernatant was centrifuged for 20 min at 12000 r/min. The human fibroblast were inoculated in 6-well culture plates, maintained at 37° C., 5% CO2. When about 50% confluence was achieved, the human fibroblast were incubated with culture medium containing plant extracts or blank control medium (culture medium containing 0.1% DMSO) for 24 h at 37° C., 5% CO2. After 24 h of incubation, total collagen was extracted. The protein concentration was determined using the Bicinchoninic Acid Protein Assay (Bio-Rad Laboratories, Hercules, Calif.) as per the manufacturer's protocol.

For immunoblot analysis, 40 μg protein was subjected to SDS-PAGE using 10% Tris-HCl gel. The protein was transferred onto a nitrocellulose membrane and blocked with 5% dry milk for 2 h and then probed with primary antibody incubated overnight at 4° C. Primary antibodies used in this study were monoclonal anti-collagen I (1:500, Abcam, Cambridge, UK) or monoclonal anti-elastin (1:200, Abcam, Cambridge, UK). The membrane was probed with an appropriate primary antibody followed by a secondary horseradish peroxidase-conjugated antibody incubated for 2 h (1:1000, Beyotime, Conn.). The protein levels were detected according to the specification of DAB Horseradish Peroxidase Color Development Kit (Beyotime, Conn.). The quantification of protein was calculated as IOD (Integral Optical Density) by a digital analysis of protein bands using IPP software. The data are expressed as the relative density of the protein normalized to β-actin. And the collagen improvement vs blank control was calculated as following formula:

> The collagen improvement vs blank control=(IOD of specific sample–IOD of blank control)/IOD of blank control×100%.

Statistical difference between the blank controls and experimental groups was determined by use of two-tailed and equal variance hypothesis student T-test and a p-value less than 0.05 was considered as significant difference.

Assay 9: ELISA Assay for Cytokines

Keratinocyte cells were plated at a concentration of $2\times10^4/cm^2$ in 6-well plates. When plating efficiency achieved about 45% per well, the keratinocytes were incubated with culture medium containing plant extracts or blank control medium (culture medium containing 0.1% DMSO) for 24 h at 37° C., 5% CO2. After 24 h incubation, supernatant was collected served for T0 time-point. Meanwhile, cells were exposed to 300 mJ/cm$^2$ of UVB radiation. Control cells were shaved but not exposed to UV. 24 h later, supernatant was collected which served as a $T_{24}$ time-point. ELISA assays (Invitrogen Ltd, IL1α: Catalog KAC1191, TNFα kit: Catalog KHC3011, IL8 kit: Catalog KHC0081, IL6 kit: Catalog KHC0061) were used to determine cytokine levels.

The inhibition of cytokine Induced by UVB Vs Blank Control equivalents which were damaged by UVB exposure, % was calculated as the following formula:

> The inhibition of cytokine Induced by UVB Vs Blank Control equivalence which were damaged by UVB exposure, %=(T24 of blank control–T24 of specific sample)/(T24 of blank control–T0 of blank control)×100%.

Statistical difference between the blank controls and experimental groups was determined by use of two-tailed and equal variance hypothesis student T-test and a p-value less than 0.05 was considered as significant difference.

The following examples illustrate the preparation and efficacy of *Ampelopsis grossedentata* extracts and *Albizia julibrissin* extracts Example 1

Preparation of *Ampelopsis grossedentata* Extract from Leaves (E1)

*Ampelopsis grossedentata* plants were collected in China. Species identification was based on gross morphological characteristics [Flora of China Editorial Committee. Flora Reipublicae Popularis Sinicae. Beijing: Science Press, 1998, 48: 53.]. Plants were cleaned of soil and debris and separated into aerial parts and roots. Approximately 1000 g of leaves were homogenized in a blender with 5000 mL of 95% ethanol/water; the suspension was maintained in constant motion for 24 hours. The resulting suspension was then filtered and dried under low pressure using a rotary evaporator not exceeding 40° C. After filtration, the left over raw material was again extracted as described above. The combined dry mass from both extractions was designated the crude extract, approximately 270 g, for a yield of 27.0% (E1).

A characteristic HPLC fingerprint of *Ampelopsis grossedentata* extract can be obtained at 292 nm with gradient elute of A (Water+0.1% formic acid): B (Acetonitrile) from 90:10 to 0:100. Dehydromyricetin was identified by HPLC-MS and quantified by HPLC-DAD. The content of dehydromyricetin in the extract is about 85.0%.

Example 2

Preparation of *Albizia julibrissin* Extract from Flowers (E2)

*Albizia julibrissin* plants were collected in China. Species identification was based on gross morphological characteristics [Flora of China Editorial Committee. Flora Reipublicae Popularis Sinicae. Beijing: Science Press, 1998, 39: 65]. Plants were cleaned of soil and debris and separated into aerial parts and roots. Approximately 2000 g of flowers were homogenized in a blender with 12,000 mL of 95% ethanol/water; the suspension was maintained in constant motion for 24 hours. The resulting suspension was then filtered and dried under low pressure using a rotary evaporator not exceeding 40° C. After filtration, the left over raw material was again extracted as described above. The combined dry mass from both extractions was designated the crude extract, approximately 144 g, for a yield of 7.2% (E2).

A characteristic HPLC fingerprint of *Albizia Julibrissin* extract can be obtained at 348 nm with gradient elute of A (Water+0.1% formic acid): B (Acetonitrile) from 90:10 to 0:100. Quercitrin was identified by HPLC-MS and quantified by HPLC-DAD. The content of Quercitrin in *Albizia Julibrissin* is about 7.74%.

Example 3

Determination of Filaggrin Protein Promotion

Extracts E1, E2 and combinations of the two at 1:1 (0.001% E1+0.001% E2) were tested for filaggrin protein levels using the method of Assay 1 described above. The crude extract was diluted with DMSO (dimethyl sulfoxide) as a 10% solution. Then the diluted extract was added to the cell culture media. Additional DMSO was added so that the concentration of the extract in the cell culture media was 0.001% by weight and the amount of DMSO was 0.1% in the cell culture media. The blank control was the 0.1% DMSO solvent by weight in the cell culture media.

The results are given in Table 1 below.

TABLE 1

Results of filaggrin protein promotion in a epidermal equivalent model

| Extract/s (wt %) | Filaggrin promotion over blank control (%) Average of Three Tests of Each Extract or Extract Combination |
|---|---|
| Blank Control | — |
| E1 (0.001) | 6.31 |
| E2 (0.001) | −2.82 |
| E1 (0.002) | 3.32 |
| E2 (0.002) | 2.96 |
| E1 + E2 (0.001 + 0.001) | 12.90* |

*$p < 0.05$ vs blank control (student T-test, two-tailed and equal variance hypothesis).

Based on these results, it can be concluded that application of the combination of *Ampelopsis grossedentata* extract and *Albizia julibrissin* extract has a synergistic effect to promote filaggrin protein of skin. Therefore, the combination of *Ampelopsis grossedentata* extract and *Albizia julibrissin* extract would be expected to have the effect to improve skin hydration and reinforce the skin barrier structure and therefore improve the skin's defense against external antigen penetration that causes skin inflammation which is involved in compromised skin problems and protect the skin from internal water loss.

Example 4

Determination of Sodium L-pyrrolidone Carboxylate (PCA) Promotion

Extracts E1, E2 and combinations of the two at 1:1, 3:1, 7:1, 1:7 weight ratios were tested for Sodium L-pyrrolidone carboxylate (PCA) levels using the method of Assay 2 described above. Each samples was tested three times.

The results are given in Table 2 below.

TABLE 2

Results of Sodium L-pyrrolidone carboxylate (PCA) and PCA promotion over blank control in an epidermal equivalent model (%)

| Extract and % | PCA μg/Tissue | PCA Promotion Vs Blank Control |
|---|---|---|
| Blank Control | 1.86 | ~ |
| E1, 0 | | |
| E2, 0 | | |
| E1, 0.00025% | 2.08 | 12.05% |
| E1, 0.0005% | 2.27 | 22.36% |
| E1, 0.001% | 2.55 | 36.98%* |
| E1, 0.0015% | 2.60 | 40.08%* |
| E1, 0.00175% | 2.74 | 47.58%* |
| E1, 0.002% | 2.82 | 51.68%* |
| E2, 0.00025% | 1.96 | 5.33% |
| E2, 0.0005% | 2.08 | 12.16% |
| E2, 0.001% | 2.67 | 43.57%* |
| E2, 0.0015% | 2.56 | 37.68%* |
| E2, 0.00175% | 2.56 | 37.94%* |
| E2, 0.002% | 2.74 | 47.29%* |
| E1, 0.002% E2, 0.002% | 4.19 | 125.62% * |
| E1, 0.0015% E2, 0.0015% | 3.42 | 83.99%* |
| E1, 0.001% E2, 0.001% | 3.52 | 89.60%* |
| E1, 0.0005% E2, 0.0005% | 2.88 | 54.99%* |
| E1, 0.00025% E2, 0.00025% | 2.41 | 29.77% |
| E1, 0.00025% E2, 0.00175% | 2.93 | 57.93%* |
| E1, 0.0015% E2, 0.0005% | 3.14 | 68.84%* |
| E1, 0.00175% E2, 0.00025% | 3.23 | 73.80%* |

*$p < 0.05$ vs blank control (student T-test, two-tailed and equal variance hypothesis).

Based on the results demonstrated in examples 3 and 4, it can be concluded that topical application of the combination of *Ampelopsis grossedentata* extract and *Albizia julibrissin* extract has a synergistic effect to promote the generation of filaggrin protein of skin and Natural Moisturizing Factors (NMFs) of the skin, thereby improving skin barrier integrity, and improving water binding capability of the skin, and thus, reducing skin inflammation which is induced by a reduction of filaggrin and improving skin hydration and relieving skin dryness.

Based on these results it can be concluded that that application of the combination of *Ampelopsis grossedentata* extract and *Albizia julibrissin* extract can improve PCA. And the application of the combination of *Ampelopsis grossedentata* extract and *Albizia julibrissin* extract has synergistic effect to promote PCA generation of skin the combination ratio is from 12.5% to 87.5% (1:7 to 7:1). The total concentration of the combination of *Ampelopsis grossedentata* extract and *Albizia julibrissin* extract can be very effective from lower to 0.0005% (W/W), to up to 30% (W/W) when considering the trans-epidermal penetration.

Example 5

Skin Equivalence Growth State Evaluation—Skin Metabolic Activity Assay

The skin metabolic activity potential for E1, E2, and combination of E1 and E2, was determined by the MTT test given in Assay 4 above.

The results are given in Table 3 below.

TABLE 3

The promotion of skin metabolic activity
In an epidermal equivalent model

| Treatment Dose, as W/W | The promotion of metabolic activity of epidermal equivalent over blank control (%) |
|---|---|
| Blank Control | — |
| E1, 0.002% | 3.23 |
| E2, 0.002% | −6.08 |
| E1 0.001% + E2 0.001% | 8.66* |

*$p < 0.05$ vs blank control (student T-test, two-tailed and equal variance hypothesis).

Based on these results, it can be concluded that by addition of *Ampelopsis grossedentata* extract to the *Albizia julibrissin* extract significantly improves skin metabolic activity which has potential to create significant higher quality of skin barrier.

Example 6

Determination of Transglutaminase-1 (TGM1) Promotion

Extracts E1, E2 and combinations of the two extracts were tested for Transglutaminase-1 (TGM1) levels using the method of Assay 3 described above.

The results are given in Table 4 below.

TABLE 4

Results of Transglutaminase-1 (TGM1) promotion over blank control in an epidermal equivalent model

| Extracts (wt. %) | TGM1 Promotion vs Blank Control |
|---|---|
| Control | — |
| E1 (0.001) | −0.45% |
| E2 (0.001) | −0.72% |
| E1 (0.002) | 2.39% |
| E2 (0.002) | 0.16% |
| E1 (0.001 + E2 (0.001) | 6.61% * |

* = $p < 0.05$ vs blank control (student T-test, two-tailed and equal variance hypothesis).

Based on these results, it can be concluded that application of the combination of *Ampelopsis grossedentata* extract and *Albizia julibrissin* extract has a synergistic effect to promote transglutaminase-1 protein of skin. Therefore, the combination of *Ampelopsis grossedentata* extract and *Albizia julibrissin* extract would be expected to have a synergistic effect to improve skin hydration and reinforce the skin barrier structure and therefore improve the skin's defense against external antigen penetration that causes skin inflammation which is involved in compromised skin problems and protect the skin from internal water loss.

Example 7

Determination of Loricrin (LOR) Promotion

Extracts E1, E2 and combinations of the two extracts were tested for Loricrin (LOR) levels using the method of Assay 5 described above. The results are given in Table 5 below.

TABLE 5

Results of Loricrin (LOR) promotion over blank control in an epidermal equivalent model

| Extracts (wt %) | LOR Promotion vs Blank Control (%) |
|---|---|
| Control | — |
| E1 (0.001) | −3.04 |
| E2 (0.001) | −6.27 |
| E1 (0.001) + E2 (0.001) | 7.60 * |

* = $p < 0.05$ vs blank control (student T-test, two-tailed and equal variance hypothesis).

Based on these results, it can be concluded that application of the combination of *ampelopsis grossedentata* extract and *Albizia Julibrissin* extract has a synergistic effect to promote loricrin protein of the skin. Therefore, the combination of *Ampelopsis grossedentata* extract and *Albizia julibrissin* extract would be expected to have synergistic effect to improve LOR protein of aged skin. Also they would be expected to improve skin hydration and reinforce the skin barrier structure and therefore improve the skin's defense against external antigen penetration that causes skin inflammation which is involved in compromised skin problems and protect the skin from internal water loss.

Example 8

Effect on Gene Expression

Extracts E1, E2 and combinations of the two extracts were tested for their effects on gene expression using the assay mentioned in Assay 7 above. The genes assayed were Loricrin (LOR), Transglutaminase-1 (TGM1), Filaggrin (FLG) and Caspase 14 (CASP14).

The results are given in Table 6 below.

TABLE 6

Effect on gene expression

| Gene expression promotion vs blank control, % | LOR | TGM1 | FLG | CASP14 |
|---|---|---|---|---|
| E2 0.00125% | −31.40% | −5.00% | 18.90% | −0.60% |
| E2 0.00125% + E1 0.00125% | 18.20% | 20.70%* | 111.90%* | 310.50%* |
| E1 0.00125% | −46.70%* | 4.20% | 46.70% | 3.00% |

*$p < 0.05$ vs blank control (student T-test, two-tailed and equal variance hypothesis).

Based on these results, it can be concluded that that application of the combination of *Ampelopsis grossedentata* extract and *Albizia julibrissin* extract can significantly improve the gene expression of FLG, Caspase-14 and TGM1. Therefore, the combination of *Ampelopsis grossedentata* extract and *Albizia julibrissin* extract would be expected to have synergistic effect to improve skin hydration and reinforce the skin barrier structure and therefore improve the skin's defense against external antigen penetration that causes skin inflammation which is involved in compromised skin problems and protect the skin from internal water loss.

Based on these results, it can be concluded that that application of the combination of *Ampelopsis grossedentata* extract and *Albizia julibrissin* extract can improve the gene expression of LOR. Therefore, the combination of *ampelopsis grossedentata* extract and *Albizia julibrissin* extract would be expected to improve LOR protein of aged skin. Also they would be expected to improve skin integrity and reinforce skin barrier structure and therefor to improve skin defense to external antigen penetration into skin to cause skin inflammation which is involved the compromised skin problems and protect skin from internal water loss.

Example 9

Determination of Skin Barrier Function by the Penetration Assay of SLS in an Epidermal Equivalence Model Skin barrier function evaluation for E1, E2, and combination of E1 and E2, was conducted by the penetration assay of SLS shown in Assay 6 above. The skin metabolic activity was tested. The results are given in Table 7 below.

TABLE 7

Results for skin barrier function evaluation using SLS penetration assay in an epidermal equivalent model

| Cell Viability (%) | Skin Metabolic Activity | |
|---|---|---|
| | 3 h | 6 h |
| E1 (0.001%) + E2 (0.001%) treated equivalents, Damaged by 1% SLS | 56.6% * | 29.66% * |
| Blank Control Equivalence, Damaged by 1% SLS | 36.88% | 12.61% |

* = $p < 0.05$ vs blank control equivalence which damaged by 1% SLS at same time point (student T-test, two-tailed and equal variance hypothesis).

Based on these results, it can be concluded that that application of the inventive combination of *ampelopsis grossedentata* extract and *albizia julibrissin* extract can create a robust skin barrier which can effectively block harmful material penetration into skin to reduce skin metabolic activity. Therefore, the combination of *ampelopsis grossedentata* extract and *albizia julibrissin* extract would be expected to have effect to increase skin integrity and reinforce skin barrier structure and improve skin hydration and reinforce the skin barrier structure and therefore improve the skin's defense against external antigen penetration that causes skin inflammation which is involved in compromised skin problems and protect the skin from internal water loss.

From the above examples 6, 7, 8 and 9 it can be seen that combinations of *Ampelopsis grossedentata* and *Albizia julibrissin* extracts would be expected to increase the hydration levels of the skin, improve the structure of stratum corneum, reinforce skin barrier structure, and reduce the penetration of outside antigens into skin thereby preventing skin cell damage, and also protect skin from internal water loss. The combination of *Ampelopsis grossedentata* and *Albizia julibrissin* extracts, thus, is capable of improving the defense to intrinsic and extrinsic stimulation, and as a consequence prevents skin allergy and inflammation, and other oxidation related compromised skin problems.

Example 10

Determination of Collagen Generation

Extracts E1, E2 and combinations of the two extracts were tested for their effect on collagen generation using the method of Assay 8 described above.

The results are given in Table 8 below.

TABLE 8

Determination of collagen generation in a human fibroblast model

| Sample | IOD of Collagen | Collagen Promotion vs blank control, % |
|---|---|---|
| Blank Control | 0.142 | — |
| E2 0.000625% | 0.144 | 1.41% |
| E2 0.00125% | 0.215 | 51.41% |
| E1 0.00125% | 0.155 | 8.80% |
| E1 0.0025% | 0.123 | −13.73% |
| E2 0.000625% + E1 0.00125% | 0.338 | 137.68%* |

*$p < 0.05$ vs blank control (student T-test, two-tailed and equal variance hypothesis).

From the above example 10 it can be seen that the inventive combination of *Ampelopsis grossedentata* and *Albizia julibrissin* extracts can significantly improve the generation of collagen, and therefore, have a synergistic effect to protect skin from aging.

Example 11

Anti-inflammation Assay for Inhibition of Cytokine Induced by UVB

Extracts E1, E2 and combinations of the two extracts were tested for their effect on anti-inflammation for inhibition of cytokines induced by UVB using the method of Assay 9 described above. The results are given in Table 9 below.

TABLE 9

Anti-inflammation Assay for Inhibition of Cytokine induced by UVB in a keratinocyte model

| Cytokine | Cytokine Induced by UVB, Inhibition Vs Control, % |
|---|---|
| IL-1α | 50.95%* |
| IL-6 | 85.00%* |
| IL-8 | 45.68%* |
| TNFα | 102.28%* |

*$p < 0.05$ vs blank control with UVB exposure (student T-test, two-tailed and equal variance hypothesis).

From the above example 11 it can be seen that the combination of *Ampelopsis grossedentata* and *Albizia julibrissin* extracts can significantly improve the inhibition of cytokines which induced by UVB exposure, and therefore, have a synergistic effect for anti-inflammation.

Example 12

A skin care composition according to the invention was prepared using the ingredients shown in Table 10.

TABLE 10

| Trade Name | INCI Name | % weight |
|---|---|---|
| Deionized Water | Water | 75.14 |
| Natrosol 250 HHR | Hydroxyethylcellulose | 0.50 |
| Citric Acid | Citric Acid | 0.06 |
| E1 | Extract of *Ampelopsis grossedentata* leaves | 0.1 |
| E2 | Extract of *Albizia julibrissin* flower | 0.1 |
| Savonol 82 | Mineral Oil | 3.00 |
| Dow Corning 345 Fluid | Cyclopentasiloxane | 2.50 |

TABLE 10-continued

| Trade Name | INCI Name | % weight |
|---|---|---|
| Dow Corning CB 9111 | Cyclopentasiloxane/Dimethicone | 2.00 |
| Dow Corning AP 8087 | Bis-Hydroxy/Methoxy Amodimethicone | 1.00 |
| Genamin BTLF | Behentrimonium Chloride | 3.0 |
| Tego Amid S18 | Stearamidopropyl Dimethylamine | 1.0 |
| Brij 721 | Steareth-21 | 0.5 |
| Lanette C18 98-100 MY | Stearyl Alcohol | 4.5 |
| Glycerin | Glycerin | 6.00 |
| Benzyl Alcohol | Benzyl Alcohol | 0.60 |

The composition shown in Table 10 was prepared as follows: water was added to a process vessel. Mixing was begun and Hydroxyethylcellulose was added and mixed until dissolved. Heat was applied and mixing continued until temperature reached 85° C. Glycerin was then added while continuing the mixing at 85° C. GENAMIN BTLF and Tego Amid S18 was added, as was Brij 721 and Lanette C18 98-100 MY, Savonol 82, and Dow Corning AP 8087. The composition was mixed at 85° C. for another 10-15 minutes. The composition was then removed from heat and continued to mix and cooled. At 40° C., Extracts of *Ampelopsis grossedentata* leaves and extract of *Albizia julibrissin* flower were added to the mixture with benzyl alcohol, Dow Corning 345 Fluid and Dow Corning CB 9111 and q.s. with water and continue to mix and cool to 30-35° C. The composition was then filled into packaging.

Example 13

A skin care composition according to the invention was prepared using the ingredients shown in Table 11.

TABLE 11

| Trade Name | INCI Name | % weight |
|---|---|---|
| Deionized Water | Water | 72.60 |
| E1 | Extract of *Ampelopsis grossedentata* leaves | 0.1 |
| E2 | Extract of *Albizia julibrissin* flower | 0.1 |
| Snow White Petrolatum | Petrolatum | 4.00 |
| Miglyol 812 | Caprylic/Capric Triglycerides | 2.50 |
| Dow Corning 9041 silicone | Dimethicone (and) Dimethicone Crosspolymer | 2.0 |
| Crodamol IPP | Isopropyl Palmitate | 3.00 |
| Uceomul GMS-165 | Glyceryl Monostearate & PEG-100 Stearate | 5.00 |
| Glycerin | Glycerin | 10.00 |
| BHT | BHT | 0.10 |
| Benzyl Alcohol | Benzyl Alcohol | 0.60 |

The composition shown in Table 10 was prepared as follows. Water was added to a process vessel and the temperature was set to 85° C. Mixing was begun and glycerin was added and mixed until dissolved. Uceomul GMS-165 and Petrolatum were added and Miglyol 812, Dow Corning 9041 silicone, and isopropyl palmitate. The composition was mixed at 85° C. for another 10-15 minutes. The composition was then removed from heat and cooled. At 40° C., benzyl alcohol and Extracts of *Ampelopsis grossedentata* leaves and extract of *Albizia julibrissin* flower were added, q.s. with water and continue to mix and cool to 30-35° C. The composition was then filled into packaging.

Example 14

A skin care composition according to the invention was prepared using the ingredients shown in Table 12.

TABLE 12

| Trade Name | INCI Name | % weight |
|---|---|---|
| Purified water | Deionized Water | 85.6 |
| E1 | Extract of *Ampelopsis grossedentata* leaves | 0.1 |
| E2 | Extract of *Albizia julibrissin* flower | 0.1 |
| HYDROLITE 5 | Pentylene glycol | 3.00 |
| Glycerin | Glycerin | 4.00 |
| Montanov L | C14-22 Alcohols & C12-20 Alkyl Glucoside | 2.00 |
| FINSOLV TN | C12-15 Alkyl Benzoate | 4.00 |
| ARISTOFLEX AVC | Ammonium Acryloyldimethyl-taurate/VP Copolymer | 1.20 |

The composition shown in Table 12 was prepared as follows. Extracts of *Ampelopsis grossedentata* leaves and extract of *Albizia julibrissin* flower were weighed and dissolved in HYDROLITE 5 as a pre-mix 1 at room temperature. Then Glycerin and deionized water was added to form Phase A with 75° C. Montanov L and FINSOLV TN were mixed to form Phase B at 75° C. Phase B was added to Phase A very slowly under continuous mixing. Mixing was continued for 15 minutes until a uniform emulsion was formed. ARISTOFLEX was added to the emulsion under continuous mixing at high speed to obtain a thick, smooth and homogenous formulation. The mixture was cooled down to 32° C. and Pre-mix 1 was added at 32° C. to create a uniform mixture.

Example 15

A skin care composition according to the invention was prepared using the ingredients shown in Table 13.

TABLE 13

| Trade Name | INCI Name | % weight |
|---|---|---|
| Purified water | Water | 83.95 |
| E1 | Extract of *Ampelopsis grossedentata* leaves | 0.1 |
| E2 | Extract of *Albizia julibrissin* flower | 0.1 |
| Pemulen TR-1 | Acrylates/C10-30 Alkyl Acrylate Crosspolymer | 0.40 |
| VERSENE NA | Disodium EDTA | 0.20 |
| Brij 72 | Steareth-2 | 0.75 |
| Brij 721 | Steareth-21 | 1.50 |
| FINSOLV TN | C12-15 Alkyl Benzoate | 4.00 |
| Dow Corning 9041 silicone | Dimethicone (and) Dimethicone Crosspolymer | 2.00 |
| Phenonip XB | Phenonip XB | 1.00 |
| Glycerin | Glycerin | 6.00 |

The composition shown in Table 13 was prepared as follows. An oil phase was prepared by adding FINSOLV TN to a clean glass beaker. Agitation was begun and the vessel was heated to 55-60° C. When the oil phase reached 55° C. or higher, Brij 72 and Brij 721 were added. When the oil phase reached 55-60° C., it was held at that temperature and mixed for 15 min (or until uniform). The temperature was then held at 55-60° C. with mixing. A water phase was prepared by adding water and Pemulen TR-1 to a clean glass beaker. Agitation was begun and the vessel was heated to 55-60° C. Disodium EDTA was added. At 55-60° C., the ingredients were mixed for 15 min or until homogeneous. The temperature was then held at 55-60° C. with mixing. The oil phase was added to the water phase with increased agitation and then mixed at high speed for 10-20 min. At 50° C. or lower, Dow Corning 9041 silicone was added. At 40° C. or lower, Phenonip XB was added. The phases were then mixed for 10 min or until uniform. Sodium hydroxide was added (target pH was 6.0). The composition was then mixed for 10 min or until uniform. Extracts of *Ampelopsis grossedentata* leaves and extract of *Albizia julibrissin* flower were weighed and dissolved in Glycerin and added to the mixture. This was mixed until uniform. Water was then added to QS and the composition was then mixed for 10 minutes.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims

What is claimed is:

1. A composition comprising an extract of *Ampelopsis grossedentata* leaves, an extract of *Albizia julibrissin* flowers and a cosmetically acceptable topical carrier, wherein the amount of the *Ampelopsis grossedentata* extract is from about 0.001% to about 10% by weight of the composition and the amount of *Albizia julibrissin* extract is from about 0.001% to about 10% by weight of the composition; wherein said composition is a skin care composition in a form selected from the group consisting of lotions, creams, serums, gels, sticks, ointments, soap bars, shampoos, hair conditioners, pastes, foams, powders, mousses, shaving creams, hydrogels, film-forming products, fluid on wipes, fluid on facial masks, and combinations of two or more thereof; and wherein the extracts are polar extracts prepared with at least one polar solvent.

2. The composition of claim 1, wherein the at least one polar solvent is selected from the group consisting of methanol, ethanol, isopropyl alcohol, n-butanol, propylene glycol, water, and mixtures thereof.

3. The composition of claim 1, wherein the weight ratio of the extracts of *Ampelopsis grossedentata* to *Albizia julibrissin* is between 1:10 to 10:1.

4. The composition of claim 1, further comprising a material selected from the group consisting of surfactants, chelating agents, emollients, humectants, conditioners, preservatives, opacifiers, fragrances, and combinations of two or more thereof.

5. The composition of claim 2, wherein the polar extract of *Ampelopsis grossedentata* is made by extracting with ethanol.

6. The composition of claim 2, wherein the polar extract of *Albizia julibrissin* is made by extracting with ethanol.

7. The composition of claim 2, wherein said composition comprises from about 0.01% to about 2% of the polar extract of *Ampelopsis grossedentata*.

8. The composition of claim 2, wherein said composition comprises from about 0.01% to about 2% of the polar extract of *Albizia julibrissin*.

9. The composition of claim 3, wherein the weight ratio of the extracts of *Ampelopsis grossedentata* to *Albizia julibrissin* is between 1:7 to 7:1.

10. The composition of claim 9, wherein the weight ratio of the extracts of *Ampelopsis grossedentata* to *Albizia julibrissin* is between 1:5 to 5:1.

11. The composition of claim 10, wherein the weight ratio of the extracts of *Ampelopsis grossedentata* to *Albizia julibrissin* is 1:1.

12. The composition of claim 1, wherein the amount of the combination of the *Ampelopsis grossedentata* extract and the *Albizia julibrissin* extract is from about 0.02% to about 10% by weight of the composition.

13. The composition of claim 1, wherein the amount of the *Ampelopsis grossedentata* extract is from about 0.01% to about 5% by weight of the composition and the amount of *Albizia julibrissin* extract is from about 0.01% to about 5% by weight of the composition.

14. A composition comprising an extract of *Ampelopsis grossedentata* leaves, an extract of *Albizia julibrissin* flowers and a cosmetically acceptable topical carrier, wherein
the amount of the *Ampelopsis grossedentata* extract is from about 0.001% to about 10% by weight of the composition,
the amount of *Albizia julibrissin* extract is from about 0.001% to about 10% by weight of the composition,
the extracts are prepared using ethanol; and
the composition is a skin care composition in a form selected from the group consisting of lotions, creams, serums, gels, sticks, ointments, soap bars, shampoos, hair conditioners, pastes, foams, powders, mousses, shaving creams, hydrogels, film-forming products, fluid on wipes, fluid on facial masks, and combinations of two or more thereof.

* * * * *